United States Patent
Song et al.

(10) Patent No.: US 9,460,823 B2
(45) Date of Patent: Oct. 4, 2016

(54) DYNAMIC BEAM APERTURE CONTROL TO REDUCE RADIATION DOSE USING COLLIMATOR

(71) Applicant: TeleSecurity Sciences, Inc., Las Vegas, NV (US)

(72) Inventors: Samuel M. Song, Las Vegas, NV (US); Junghyun Kwon, Las Vegas, NV (US); Jongkyu Lee, Las Vegas, NV (US); Douglas P. Boyd, Las Vegas, NV (US)

(73) Assignee: TELESECURITY SCIENCES, INC., Las Vegas, NV (US)

( * ) Notice: Subject to any disclaimer, the term of this patent is extended or adjusted under 35 U.S.C. 154(b) by 346 days.

(21) Appl. No.: 14/023,346

(22) Filed: Sep. 10, 2013

(65) Prior Publication Data

US 2014/0086380 A1 Mar. 27, 2014

Related U.S. Application Data

(60) Provisional application No. 61/699,140, filed on Sep. 10, 2012.

(51) Int. Cl.

| | |
|---|---|
| *A61B 6/02* | (2006.01) |
| *G21K 1/04* | (2006.01) |
| *H05K 7/20* | (2006.01) |
| *F28F 3/00* | (2006.01) |
| *A61B 6/10* | (2006.01) |
| *G06F 1/20* | (2006.01) |
| *G06F 1/16* | (2006.01) |
| *H01L 23/373* | (2006.01) |
| *A61B 6/03* | (2006.01) |
| *A61B 6/06* | (2006.01) |
| *A61B 6/00* | (2006.01) |
| *A61B 8/00* | (2006.01) |

(52) U.S. Cl.
CPC ............... *G21K 1/046* (2013.01); *A61B 6/032* (2013.01); *A61B 6/06* (2013.01); *A61B 6/10* (2013.01); *A61B 6/4028* (2013.01); *A61B 8/54* (2013.01); *F28F 3/00* (2013.01); *G06F 1/1656* (2013.01); *G06F 1/20* (2013.01); *H01L 23/373* (2013.01); *H01L 23/3733* (2013.01); *H01L 23/3735* (2013.01); *H05K 7/2039* (2013.01); *H01L 2924/0002* (2013.01); *Y10T 428/2848* (2015.01)

(58) Field of Classification Search
CPC ... A61B 6/4028; A61N 5/1045; G21K 1/046
See application file for complete search history.

(56) References Cited

U.S. PATENT DOCUMENTS

| | | | | |
|---|---|---|---|---|
| 7,082,182 B2 * | 7/2006 | Zhou | ...................... | A61B 6/032 378/10 |
| 7,428,297 B2 * | 9/2008 | Eilbert | ............... | G01N 23/2252 378/10 |
| 8,565,377 B2 * | 10/2013 | Robar | .................. | A61N 5/1049 378/62 |
| 2013/0336562 A1 * | 12/2013 | Zamyatin | .............. | G06T 11/006 382/131 |

* cited by examiner

*Primary Examiner* — David J Makiya
*Assistant Examiner* — Dani Fox
(74) *Attorney, Agent, or Firm* — Procopio, Cory, Hargreaves & Savitch, LLP

(57) ABSTRACT

A computed tomography (CT) apparatus including: an X-ray source configured to direct X-rays toward a detector assembly; a dynamic beam collimator fixed in space and configured to dynamically limit an X-ray beam directed toward an object of interest, the dynamic beam collimator including a plurality of leaflets to block a cone beam of X-rays impinging upon the dynamic beam collimator, wherein a subset of the plurality of leaflets opens and closes to block or allow a portion of the cone beam of X-rays to reduce or increase a solid angle of the cone beam, wherein the cone beam of X-rays with the reduced solid angle is directed toward a predetermined portion of the object of interest; and the detector assembly configured to detect the directed cone beam of X-rays on a side opposite to the X-ray source.

6 Claims, 21 Drawing Sheets

Multi Leaf Collimator

Six DOF Collimator

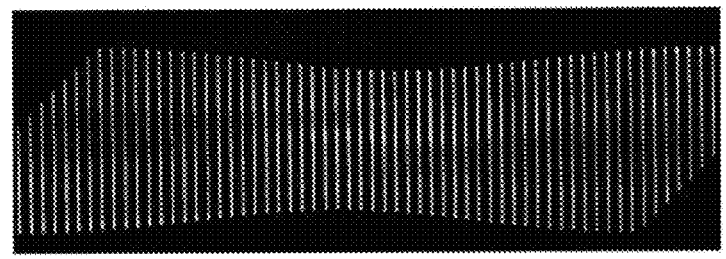
FIG. 20a
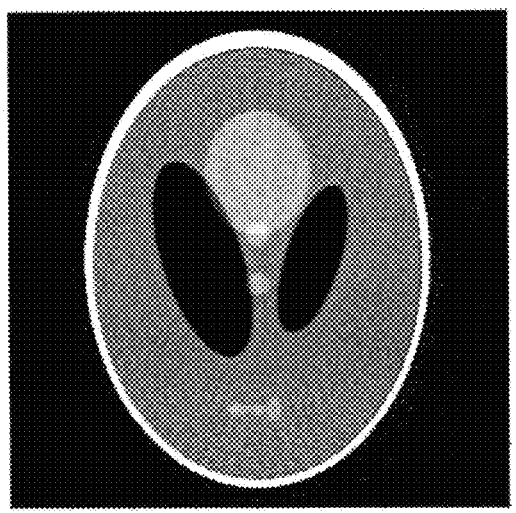 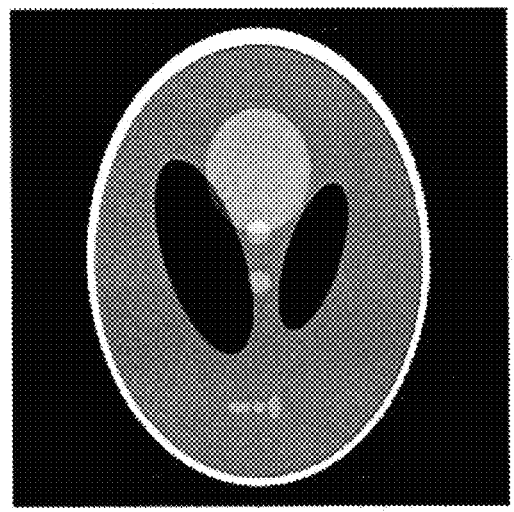
FIG. 20b          FIG. 20c

DYNAMIC BEAM APERTURE CONTROL TO REDUCE RADIATION DOSE USING COLLIMATOR

CROSS-REFERENCE TO RELATED APPLICATIONS

This application claims the benefit of priority under 35 U.S.C. §119(e) of U.S. Provisional Patent Application No. 61/699,140, filed Sep. 10, 2012, entitled "Sub-mSv Compressed Sensing and Dynamic Beam Aperture Control". The disclosure of the above-referenced application is incorporated herein by reference.

BACKGROUND

1. Field of the Invention

The present invention relates to reducing radiation dose in X-ray Computed Tomography (CT) scanning by dynamic beam aperture control, and more specifically, to reducing radiation dose in X-ray CT scanning using collimators that can dynamically control the beam aperture.

2. Background

The annual number of CT exams has already surpassed 70 million in the US and this number is expected to increase even further. Although the radiation from CT exam is generally agreed to be weak, with a very small probability of causing cancer to patients, when this small probability is applied to tens of millions of CT exams, the total number of affected people can be quite significant. In fact, the controversial study of Brenner estimates that 0.4% to 2.0% of all new cancer cases may be attributed to CT radiation. In addition to this study, other studies claim that even though CT exams only make up 12% of all diagnostic radiological exams, the CT exams are responsible for over 45% of radiation exposure. While one may question the relevance of these statistics, one cannot deny the fact that ionizing radiation can be hazardous to your health and unnecessary exposure to radiation must be avoided at all times.

SUMMARY

The present invention discloses apparatuses for reducing radiation dose in X-ray CT scanning by dynamically controlling the beam aperture.

In one aspect, apparatuses to reduce radiation dose of electron beam computed tomography (EBCT) scanners are disclosed. The apparatuses include Dynamic Beam Collimator and Multi Slit Collimator. The Dynamic Beam Collimator is composed of tantalum leaflets, which are individually controlled to dynamically adjust the beam aperture as the electron beam moves on the tungsten target. The Dynamic Beam Collimator can be controlled in order to provide projection data necessary for both the Interior Tomography and Sparse-view Tomography. The Multi Slit Collimator is a ring composed of multiple slits, each of which provides one source-fan worth of data. The Multi Slit Collimator can be used for the Sparse-view Tomography as it enables to radiate a patient only at a controlled number of X-ray source positions.

In another aspect, apparatuses to reduce radiation dose for mechanical CT scanners and breast CT scanners are disclosed. The apparatuses include Multi Leaf Collimator and Six Degrees Of Freedom (DOF) Collimator. The Multi Leaf Collimator, which is composed of tantalum leaflets and housing, is coupled to the X-ray tube and modulates the beam aperture by controlling its leaflets as it moves together with the X-ray tube. The Six DOF Collimator, which is composed of a plate with a hole and driving mechanism, is attached to the X-ray tube and modulates the beam aperture by controlling the 3-D pose of the plate using the driving mechanism as it moves together with the X-ray tube. Both the Multi Leaf Collimator and Six DOF Collimator can be used for the Interior Tomography and Sparse-view Tomography.

BRIEF DESCRIPTION OF THE DRAWINGS

The details of the present invention, both as to its structure and operation, may be gleaned in part by study of the appended further drawings, in which like reference numerals refer to like parts, and in which:

FIG. 20a shows the fan-beam sinogram obtained with the Multi Slit Collimator.

FIG. 20b shows the reconstruction result using the sinogram in FIG. 20a by SART.

FIG. 20c shows the reconstruction result using the sinogram in FIG. 20a by SART with TV minimization.

DETAILED DESCRIPTION

Figure 1:
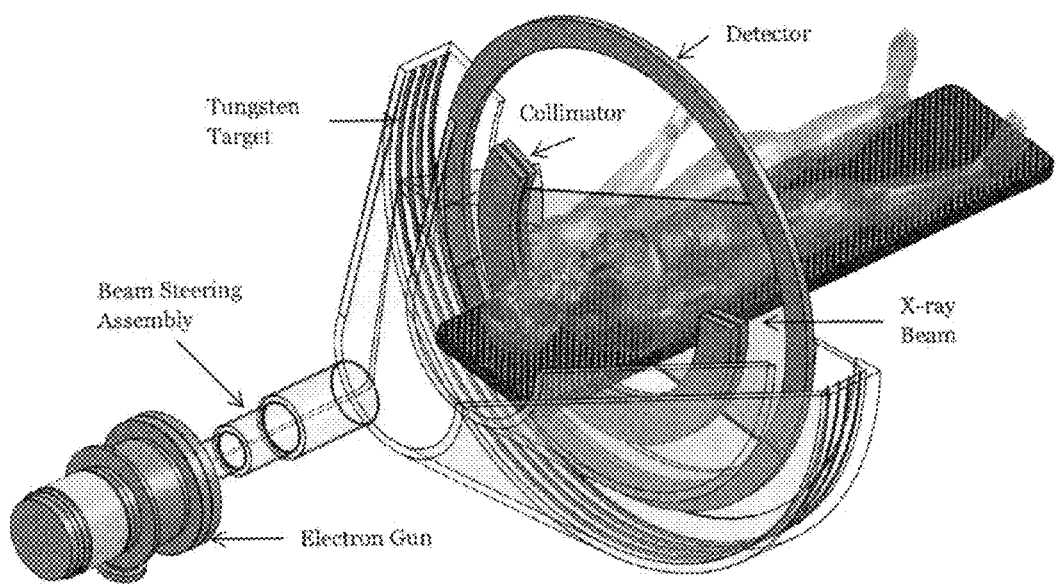
FIG. 1 shows one embodiment of an EBCT scanner.

There are two possible approaches to reducing radiation dose in X-ray CT scanning: 1) Interior Tomography; and 2) Sparse-view (or few-view) Tomography. In the Interior Tomography, only the interior part of a patient, which is of interest, is radiated by X-rays and only the radiated interior part is reconstructed accordingly. In the Sparse-view Tomography, the projection data of a patient is obtained with much sparser views than the usual projection data. Previously, the general understanding was it is difficult to obtain clinically viable images with sufficient image quality (IQ) by the Sparse-view Tomography and Interior Tomography using conventional reconstruction algorithms such as the filtered Back-projection (FBP) and algebraic reconstruction technique (ART). However, recent technical advancements show some possibility of solving this seemingly difficult task.

Recent developments in compressed sensing show that appropriate sampling strategies (i.e., compressed sensing) for systems with a sparse basis may provide enough information so that the original system (or image) can be reconstructed with enough accuracy. These works in compressed sensing minimizes the L1-norm of the gradient magnitude, which in fact is equivalent to minimizing the Total Variation (TV). The concept of compressed sensing/TV minimization, together with recent advances in reconstruction algorithms has shown that image reconstruction through recent algorithms for the Interior Tomography and Sparse-view Tomography can provide clinically viable images.

Reduction of radiation dose while maintaining IQ by the advanced reconstruction algorithms based on the compressed sensing/TV minimization for the Interior Tomography and Sparse-view Tomography will revolutionize the current practice of CT exams. The heart patient would be prescribed the Interior Tomography (of the heart) with minimal exposure to surrounding tissue to reduce the dose by a factor two to four. All screening CT exams will be performed using the Sparse-view Tomography with the dose reduction of a factor 5 to 10 or even more.

However, all studies related to the Interior Tomography and Sparse-view Tomography and references therein do not mention the design of actual hardware to collect the necessary data at the lower dose. The algorithms have been tested by simulating projections and/or artificially extracting the necessary portion from projections obtained from conventional CT scanners. Therefore, for the actual deployment of the Interior Tomography and Sparse-view Tomography at clinics, it is necessary to design and develop actual hardware to enable the collection of the necessary data for the Interior Tomography and Sparse-view Tomography at the lower dose.

Certain embodiments as disclosed herein provide for reducing radiation dose in X-ray CT scanning by dynamically controlling the beam aperture. After reading the below description it will become apparent how to implement the invention in various embodiments and applications. However, although various embodiments of the present invention will be described herein, it is understood that these embodiments are presented by way of example only, and not limitation. As such, this detailed description of various embodiments should not be construed to limit the scope or breadth of the present invention.

Dynamic Beam Collimator for EBCT Scanners

FIG. 1 shows an EBCT scanner mainly used for cardiac CT scanning. The electron beam from the electron gun is steered by the beam steering assembly toward the tungsten target ring and moves at a constant speed along the target ring. Since X-rays are generated as the electron beam hits the target ring, fan beam projections at numerous source positions encompassing 180 degrees plus fan angle, which are required to perfectly reconstruct the scanned object, can be obtained.

Figure 2A:
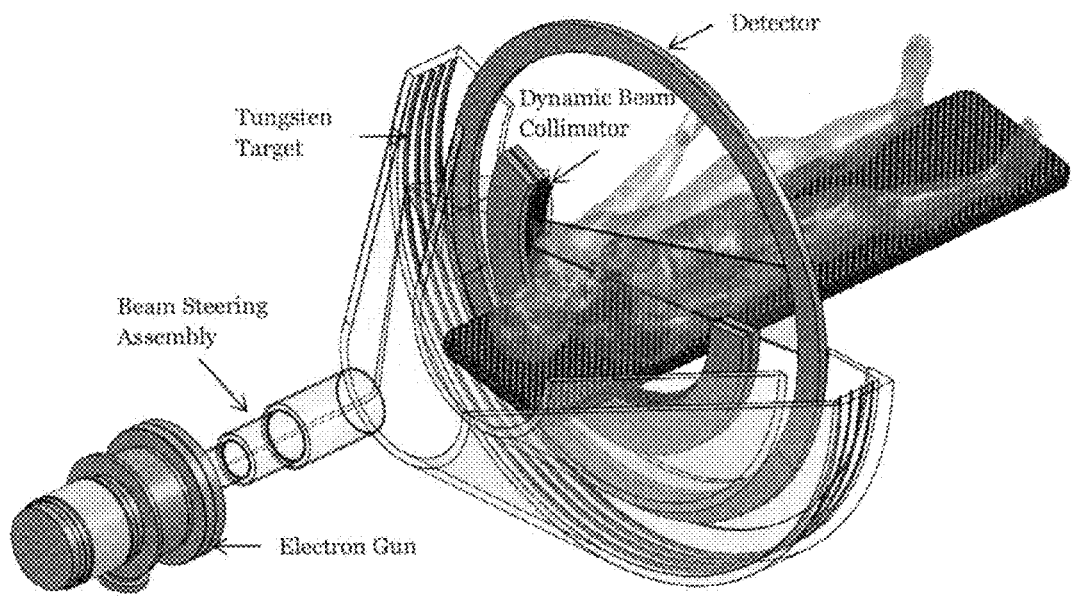
FIGS. 2a and 2b show a Dynamic Beam Collimator attached to the EBCT scanner which partially blocks the X-ray fan beam to radiate only the region of interest (ROI).
Figure 2B:
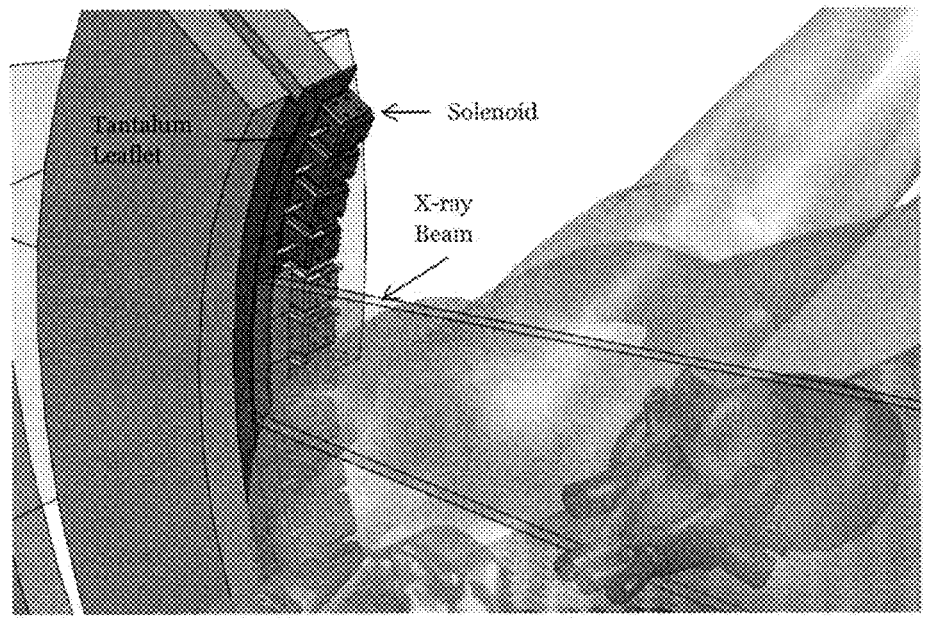

FIGS. 2a and 2b show the details of a Dynamic Beam Collimator attached to the EBCT scanner. The Dynamic Beam Collimator is composed of tantalum leaflets that are individually controlled to dynamically modulate the beam aperture as the electron beam moves along the tungsten target ring. FIG. 2a shows the partially blocked fan beam exposing only the heart for the Interior Tomography. The X-ray beam outside the heart is blocked by a series of tantalum leaflets attached to a solenoid, whose position is synchronized to the position of the electron beam. As the electron beam moves on the tungsten target, the appropriate solenoids will engage the attached tantalum leaflet to only expose the heart. The radiated region for the Interior Tomography does not have to be the central region. FIG. 2b shows the zoomed image of the Dynamic Beam Collimator in FIG. 2a. In FIG. 2b, all tantalum leaflets are closed except for the three solenoids beginning from the solenoid #5 from the top. The opening of three tantalum leaflets is enough to expose the heart in its entirety. This would reduce the dose by a factor 2 to 4.

Figure 3A:
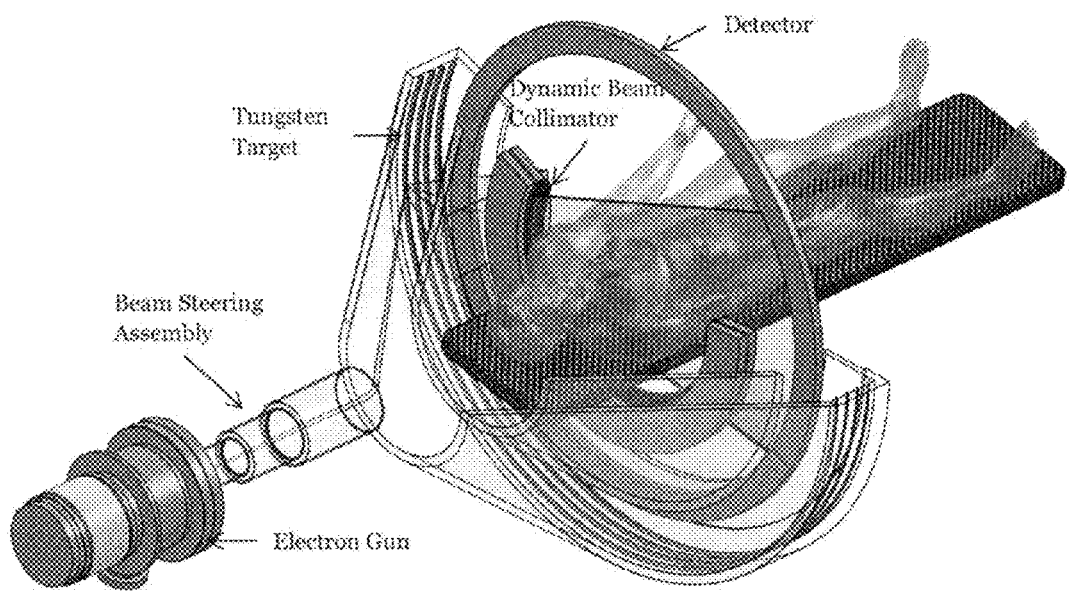
FIGS. 3a and 3b show the Dynamic Beam Collimator attached to the EBCT scanner which does not block the X-ray fan beam.
Figure 3B:
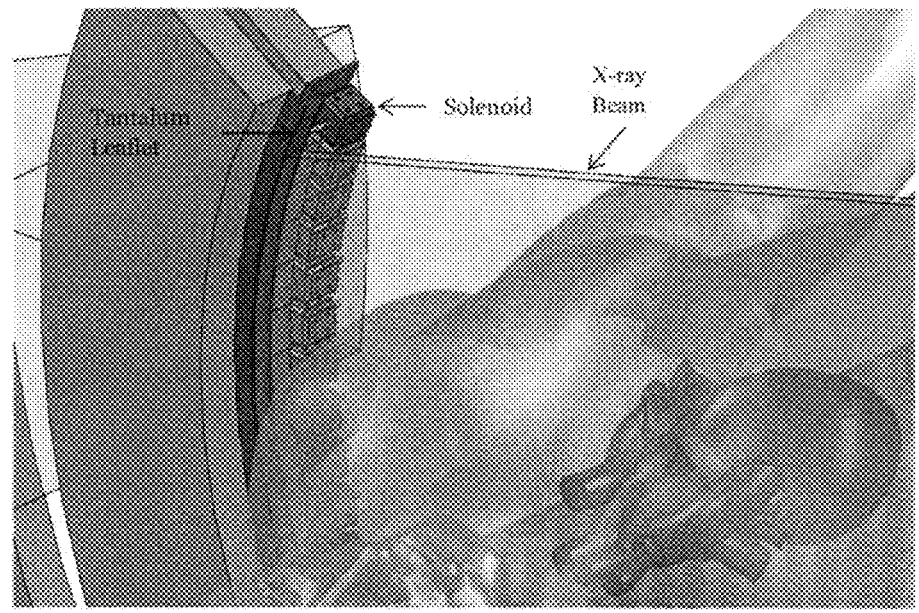
Figure 4A:
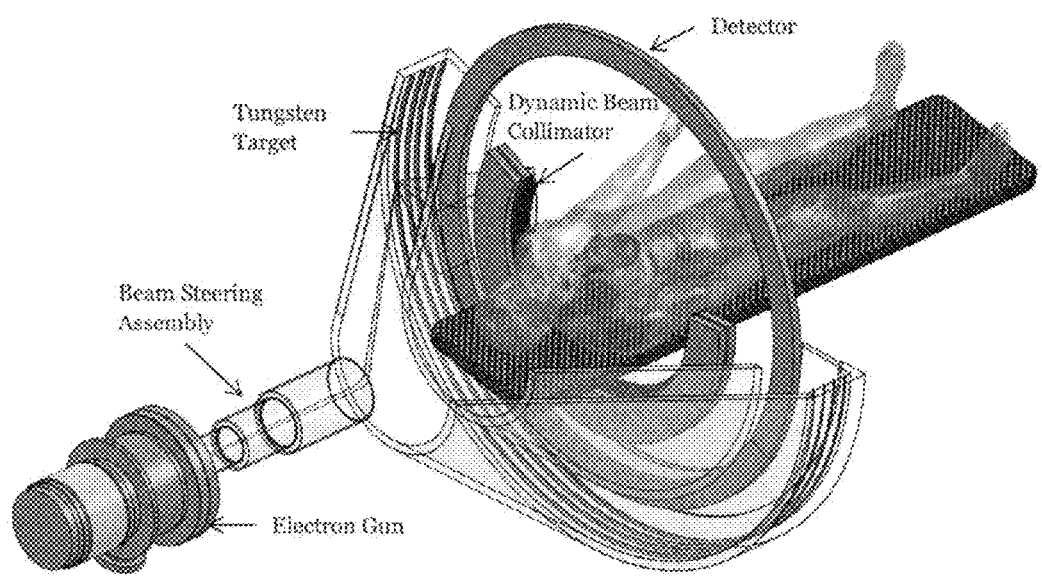
FIGS. 4a and 4b show the Dynamic Beam Collimator attached to the EBCT scanner which completely blocks the X-ray fan beam.
Figure 4B:
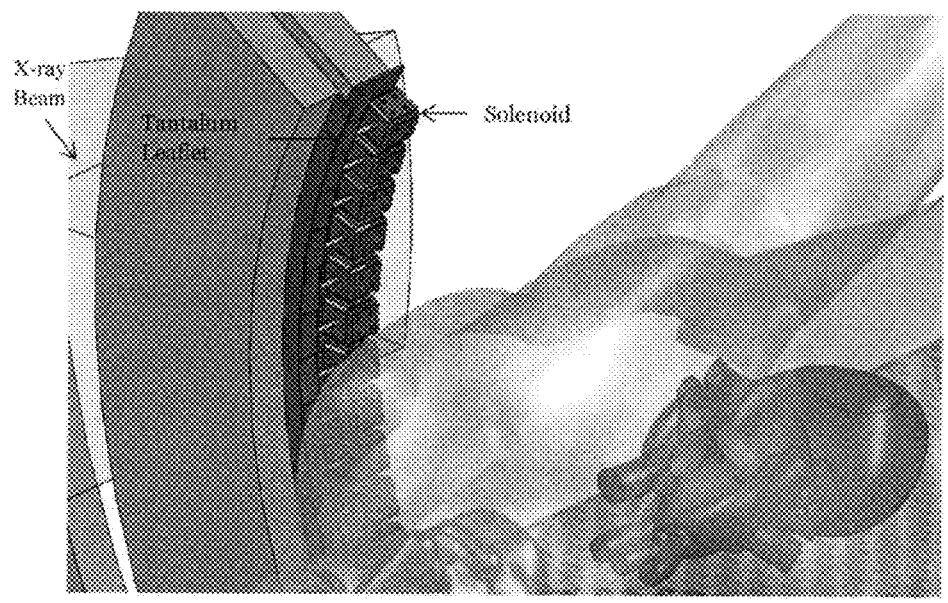

The Dynamic Beam Collimator also can be used for the Sparse-view Tomography. FIG. 3a shows the X-ray fan beam completely unblocked by the Dynamic Beam Collimator. FIG. 3b shows the zoomed image of the Dynamic Beam Collimator in FIG. 3a. In FIG. 3b, nine tantalum leaflets from the solenoid #2 from the top are open to pass the entire X-ray fan beam without blocking. FIG. 4a shows the X-ray fan beam completely blocked by the Dynamic Beam Collimator with all leaflets closed. FIG. 4b shows the zoomed image of the Dynamic Beam Collimator in FIG. 4a. By passing the entire X-ray fan beams only at the specific source locations as in FIGS. 3a and 3b while completely blocking X-ray fan beams at the other locations as in FIGS. 4a and 4b, projection data necessary for the Sparse-view Tomography can be obtained with the reduced radiation dose.

Multi Slit Collimator for EBCT Scanners

Figure 5A:
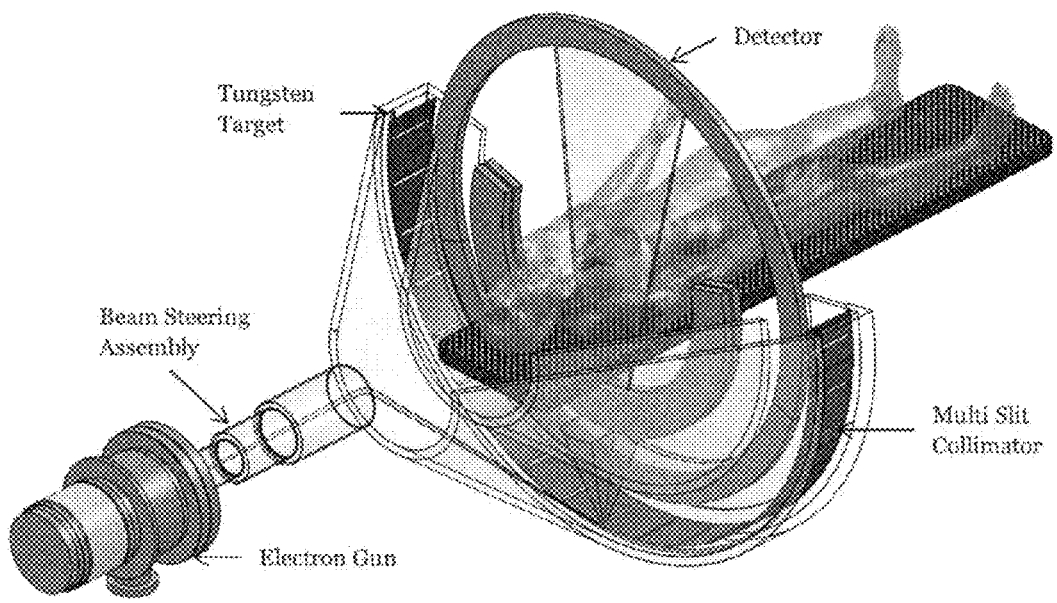
FIGS. 5a and 5b show a Multi Slit Collimator attached to the EBCT scanner to allow illumination at the view angles determined by the location of the slits.
Figure 5B:
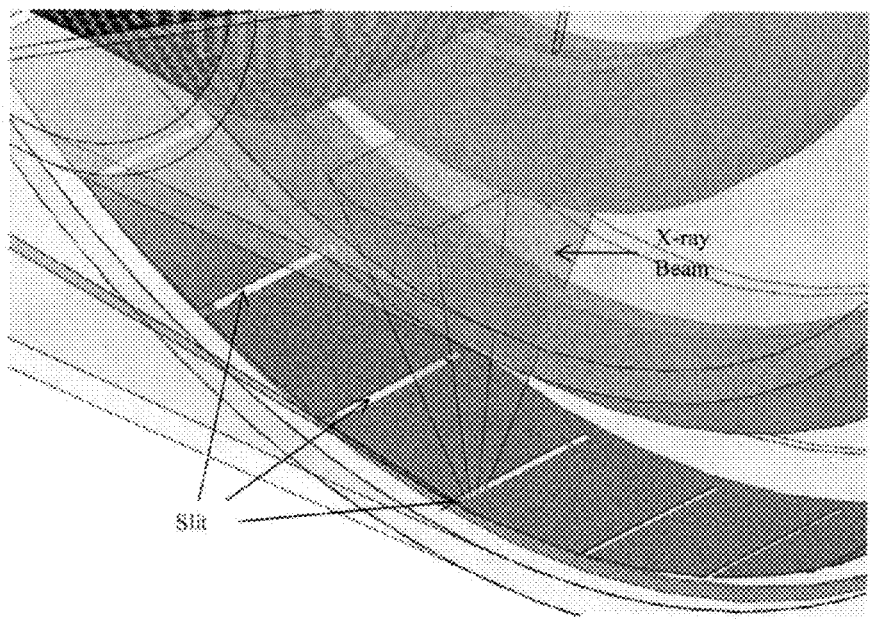

FIGS. 5a and 5b show the details of a Multi Slit Collimator attached to the EBCT scanner. The Multi Slit Collimator is a ring composed of multiple slits. Due to the steering of the electron beam, a source-fan data can be collected while the electron beam traverses by the slit as FIG. 5a shows. FIG. 5b is the zoomed image of the Multi Slit Collimator in FIG. 5a. The size of the slit can be set, for instance, so that a single 30 degree X-ray source-fan is formed when the electron beam is closest to the slit. A Multi Slit Collimator with 60 slits would reduce the dose by a factor 5 compared to the full exposure case without the Multi Slit Collimator. The projection data obtained with the Multi Slit Collimator can be used for the Sparse-view Tomography.

Multi Leaf Collimator for Mechanical CT Scanners

Figure 6A:
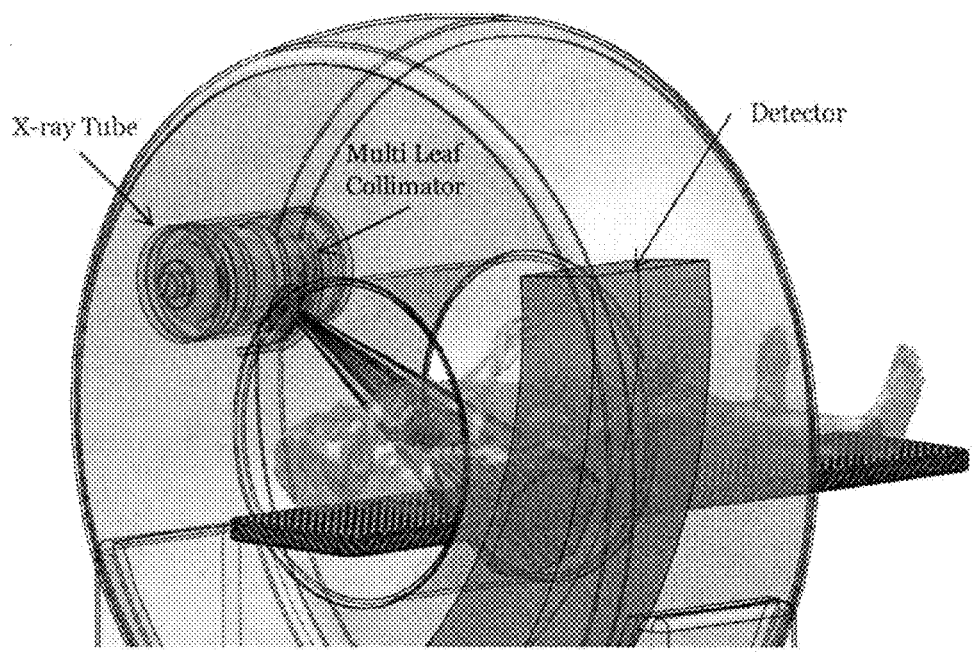
FIGS. 6a and 6b show a Multi Leaf Collimator attached to a mechanical CT scanner which partially blocks the X-ray cone beam to radiate only the ROI.
Figure 6B:
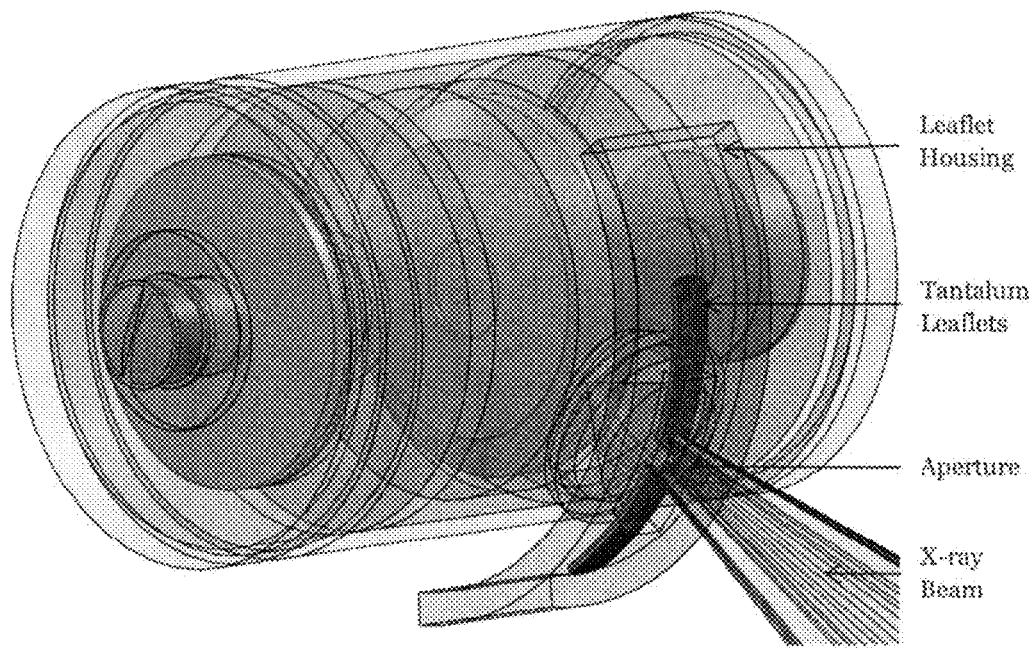

Mechanical CT scanners are most commonly used in clinics, in which an X-ray tube generating X-ray cone beams circularly rotates to radiate patients from various angles. FIGS. 6a and 6b show the details of a Multi Leaf Collimator to dynamically modulate the beam aperture of mechanical CT scanners. The Multi Leaf Collimator is coupled to the X-ray tube and moves together as it rotates. The Multi Leaf Collimator is mainly composed of tantalum leaflets and leaflet housing. Inside of the leaflet housing that is coupled to the X-ray tube, thin leaflets are stacked longitudinally and controlled to modulate the beam aperture. FIG. 6a shows the X-ray cone beam shaped by the Multi Leaf Collimator to radiate only the ROI. FIG. 6b is the zoomed image of the Multi Leaf Collimator in FIG. 6a. As FIG. 6b shows, the tantalum leaflets move longitudinally to shape the beam aperture appropriately. The projection data obtained with the shaped X-ray cone beams as the one in FIGS. 6a and 6b can be used for the Interior Tomography.

Figure 7A:
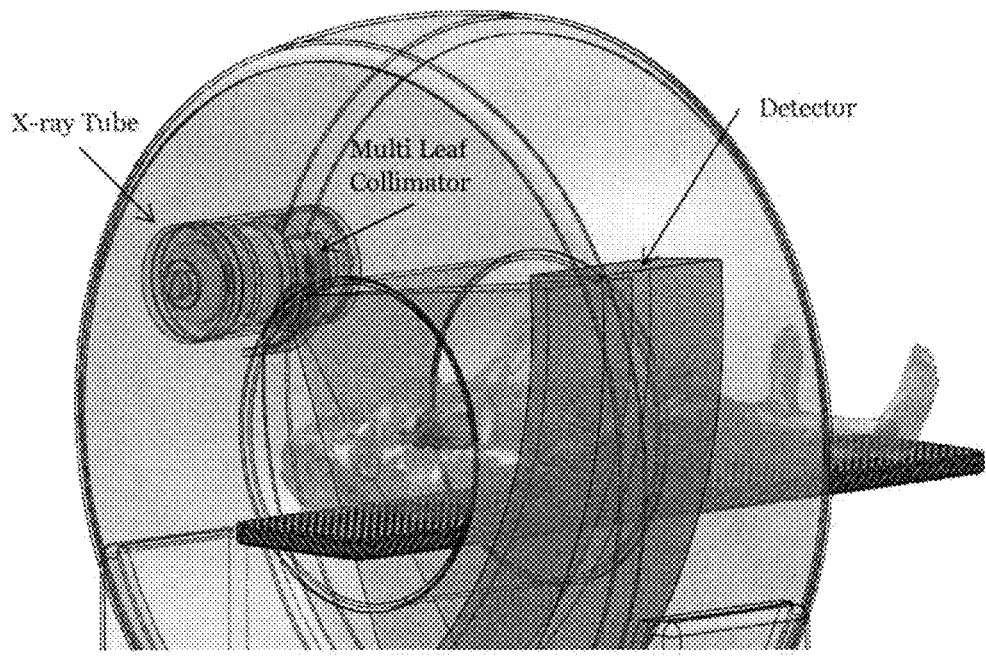
FIGS. 7a and 7b show a Multi Leaf Collimator attached to a mechanical CT scanner which does not block the X-ray cone beam.
Figure 7B:
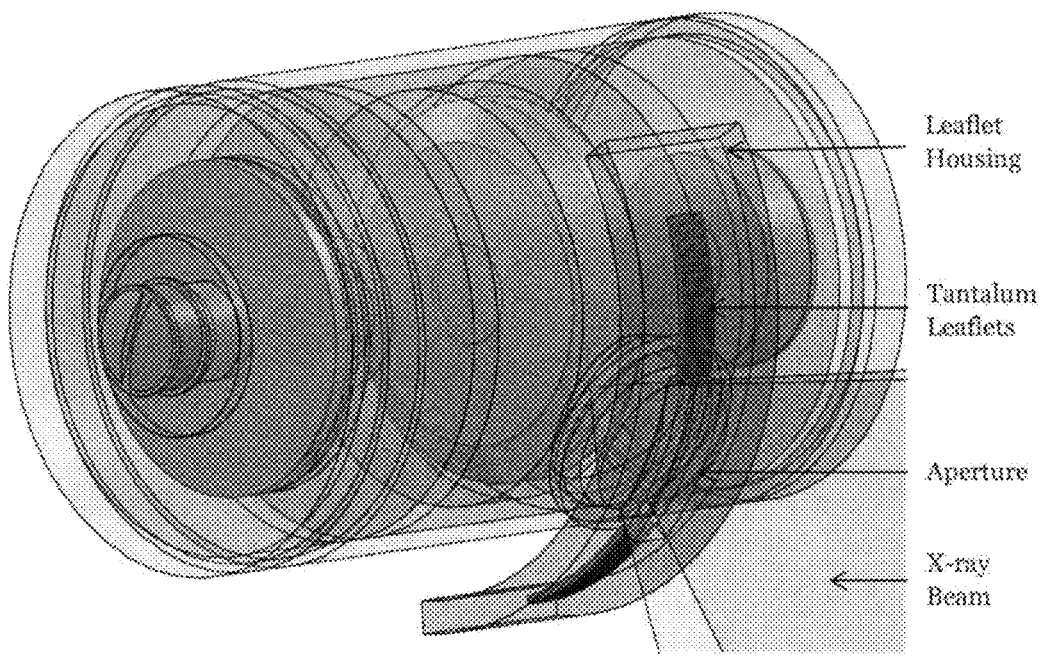
Figure 8A:
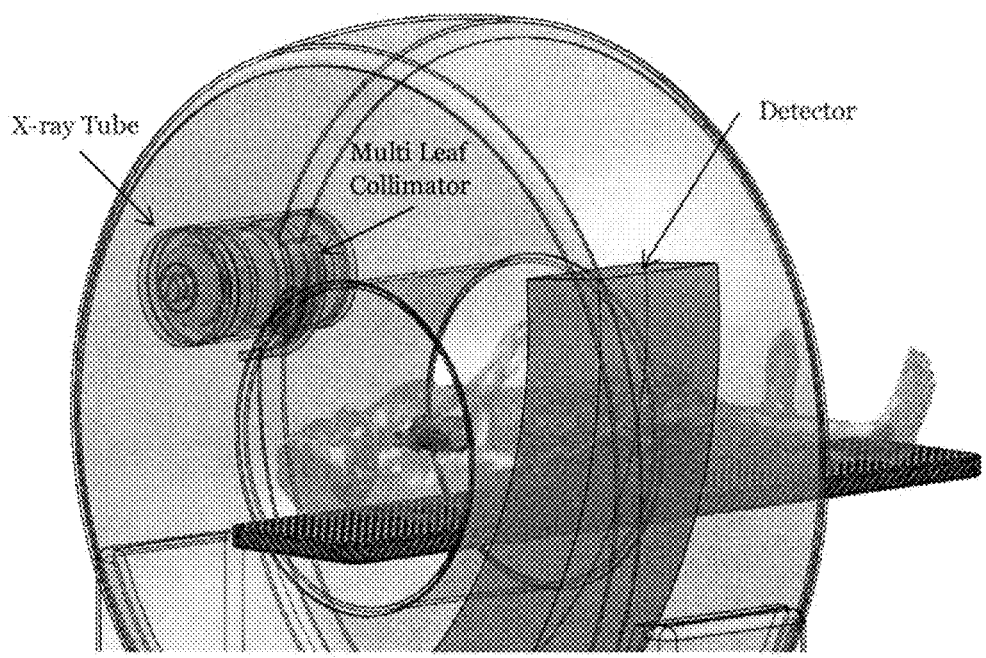
FIGS. 8a and 8b show a Multi Leaf Collimator attached to a mechanical CT scanner which completely blocks the X-ray cone beam.
Figure 8B:
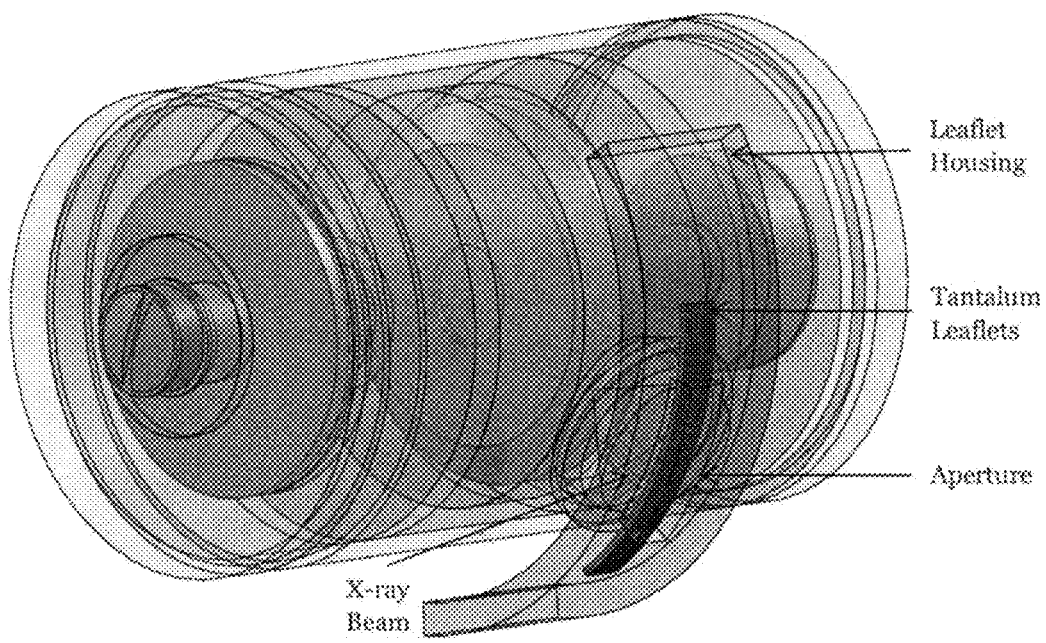

The Multi Leaf Collimator also can be used for the Sparse-view Tomography. FIG. 7a shows the X-ray cone beam completely unblocked by the Multi Leaf Collimator with the beam aperture fully open. FIG. 7b is the zoomed image of the Multi Leaf Collimator in FIG. 7a. FIG. 8a shows the X-ray cone beam completely blocked by the Multi Leaf Collimator with the beam aperture fully closed. FIG. 8b is the zoomed image of the Multi Leaf Collimator in FIG. 8b. By dynamically controlling the leaflets of the Multi Leaf Collimator to fully open the beam aperture only at the specific source locations as in FIGS. 7a and 7b while completely blocking X-ray fan beams at the other locations as in FIGS. 8a and 8b, projection data necessary for the Sparse-view Tomography can be obtained with the reduced radiation dose.

Six DOF Collimator for Mechanical CT Scanners

Figure 9A:
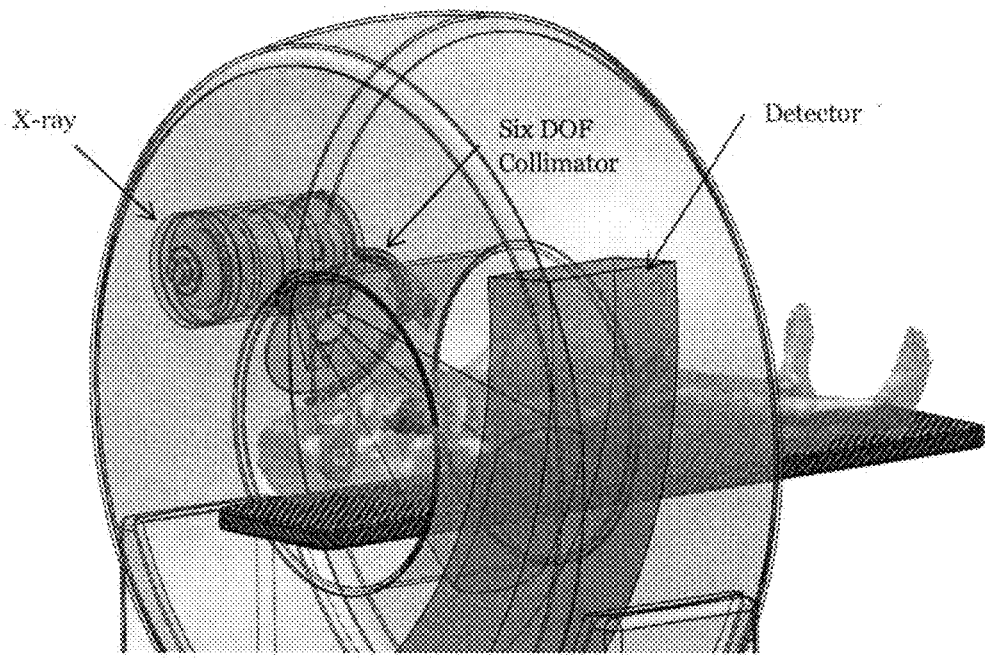
FIGS. 9a and 9b show a Six DOF Collimator attached to a mechanical CT scanner which partially blocks the X-ray cone beam to radiate only the ROI.
Figure 9B:
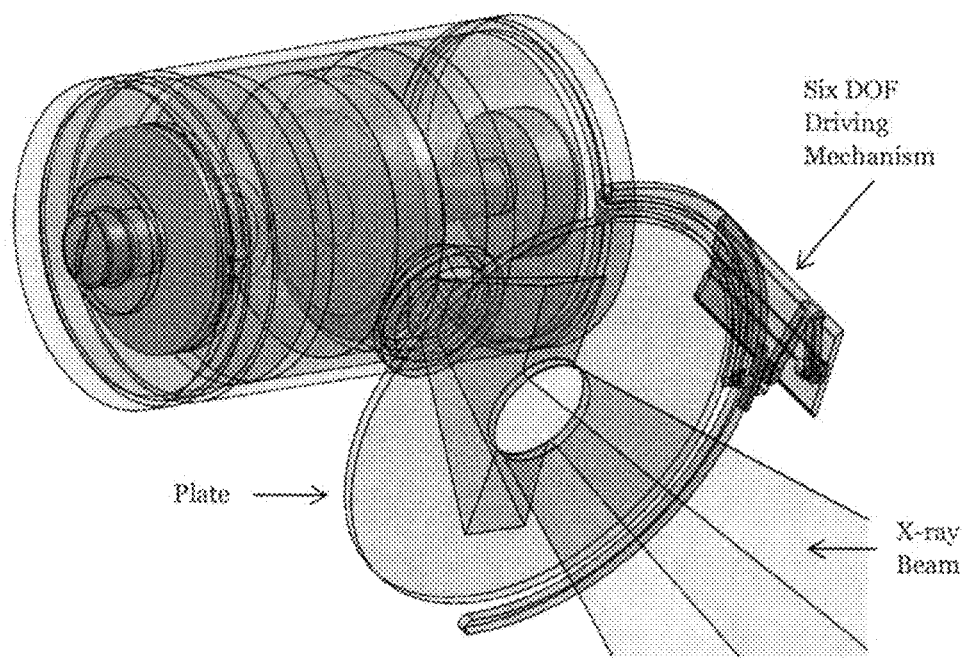

As a simple alternative to the Multi Leaf Collimator for Mechanical CT scanners, the Six DOF Collimator shown in FIGS. 9a and 9b dynamically adjusts the beam aperture by controlling the 3-D pose of a plate with a hole in front of the X-ray tube. FIG. 9a shows the details of a Six DOF Collimator attached to the X-ray tube of the mechanical CT scanner. FIG. 9b is the zoomed image of the Six DOF Collimator in FIG. 9a. The Six DOF Collimator is composed of the plate that blocks all X-rays except those passing through the hole and driving mechanism that controls the 3-D pose of the plate. The six DOF driving mechanism of the Six DOF Collimator is mainly composed of two parts, one for the 3 DOF rotational motion and the other for the 3 DOF translational motion. The rotational motion part is composed of circular frames and rotational joints and enables the 3-D rotation of the plate centered at the hole. The translational part is composed of a sliding rail and two-link arm. The sliding rail generates the linear movement of the plate along the direction parallel to the central X-ray and controls the scale of the beam aperture. The two-link arm generates the 2-D translation motion in the plane perpendicular to the central X-ray. By using this driving mechanism, the plate can be controlled in 6 DOF. Any driving mechanisms that can control the 6 DOF motion of the plate can be used instead.

By controlling the 3-D pose of the plate by the driving mechanism, the shape of the X-ray beam that passes through the hole can be adjusted. When the plate is far from the X-ray tube as FIGS. 9a and 9b, a very small portion of X-rays can pass through the hole and thus only the ROI can be radiated for the Interior Tomography.

Figure 10A:
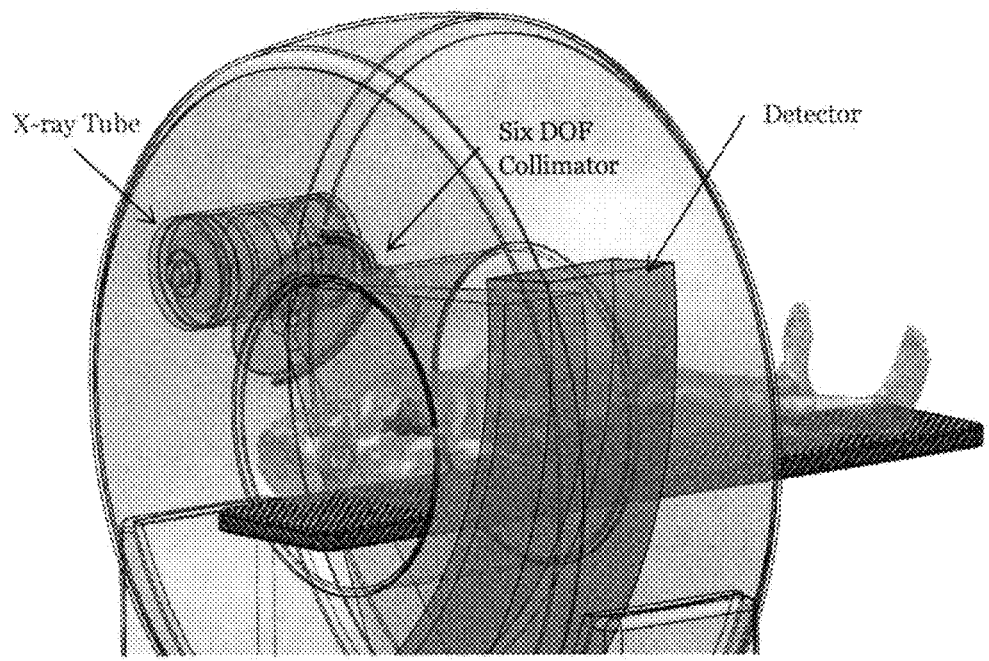
FIGS. 10a and 10b show a Six DOF Collimator attached to a mechanical CT scanner which does not block the X-ray cone beam.
Figure 10B:
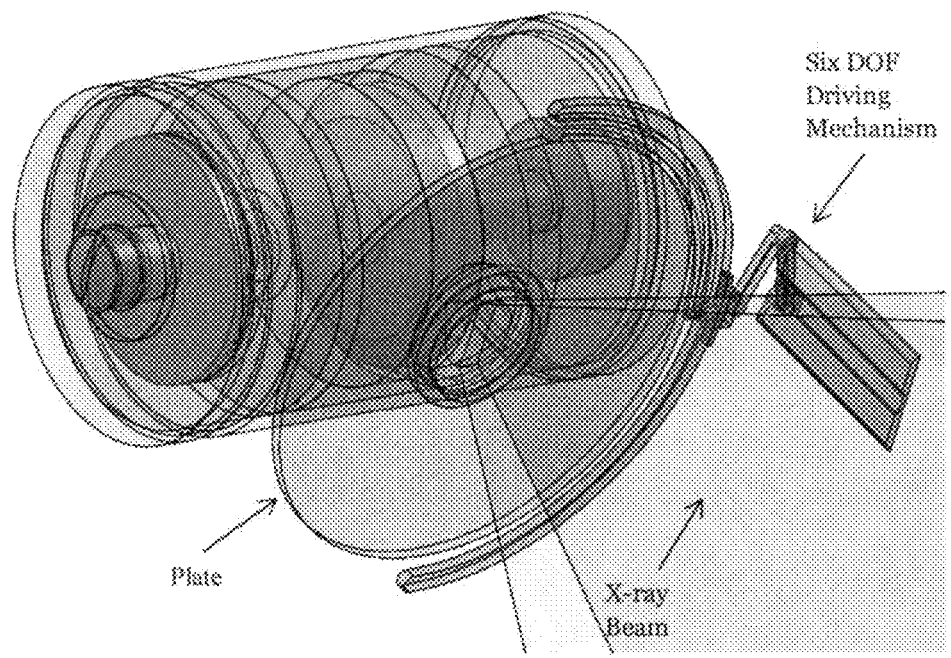
Figure 11A:
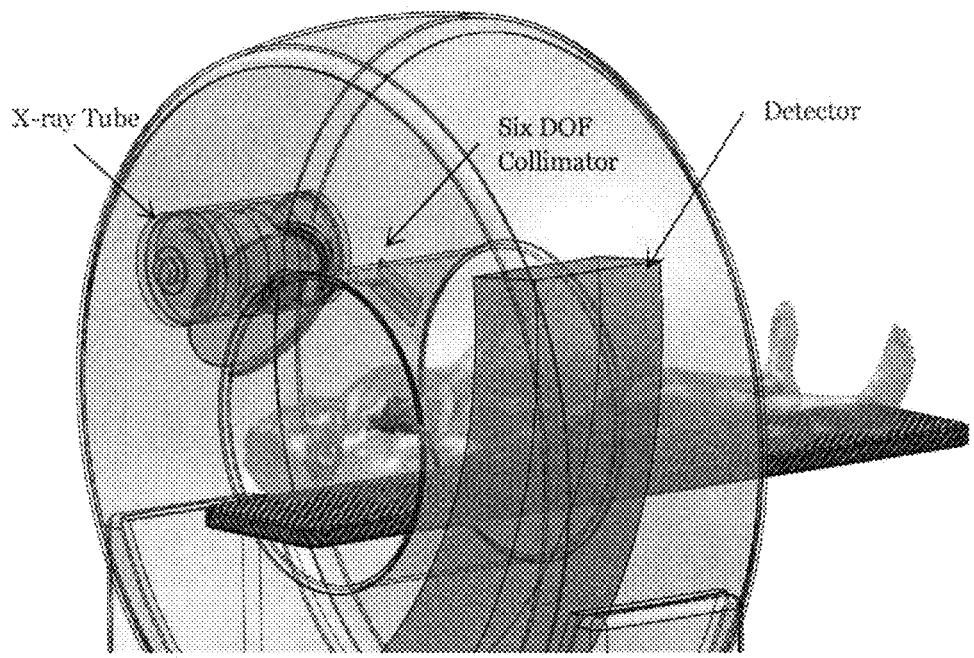
FIGS. 11a-b show a Six DOF Collimator attached to a mechanical CT scanner which completely blocks the X-ray cone beam.
Figure 11B:
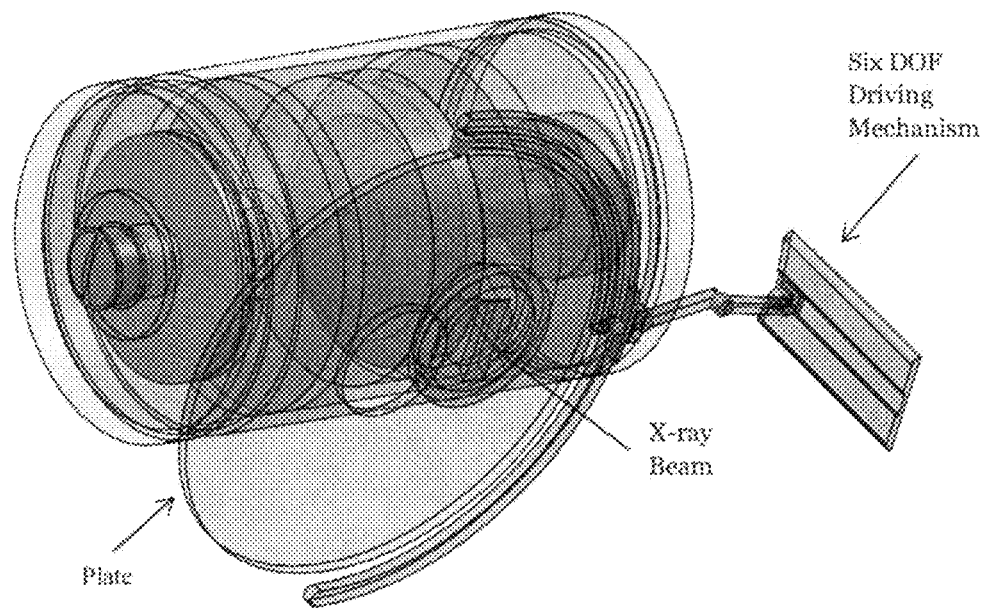

When the plate is quite close to the X-ray tube as FIGS. 10a and 10b, all X-rays can pass through the hole without being blocked. FIG. 10b is the zoomed image of the Six DOF Collimator in FIG. 10a. If the plate is quite close to the X-ray tube and off centered from the central X-ray as FIGS. 11a and 11b, it can block all X-rays. FIG. 11b is the zoomed image of the Six DOF Collimator in FIG. 11a. Therefore, we can obtain the projection data necessary for the Sparse-view Tomography by blocking all X-rays at all source positions using the plate as FIGS. 11a and 11b except some specific source positions where no X-rays are blocked by the plate as FIGS. 10a and 10b.

Figure 12A:
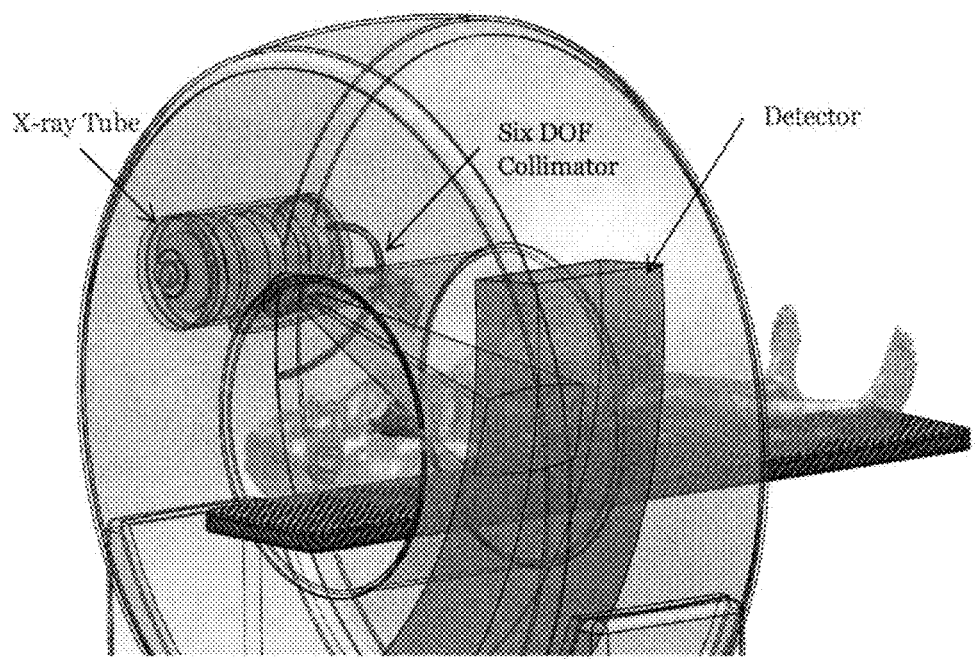
FIGS. 12a and 12b show a Six DOF Collimator attached to a mechanical CT scanner which makes the X-ray cone beam narrower to radiate only the ROI, different from the ROI of FIGS. 9a and 9b.
Figure 12B:
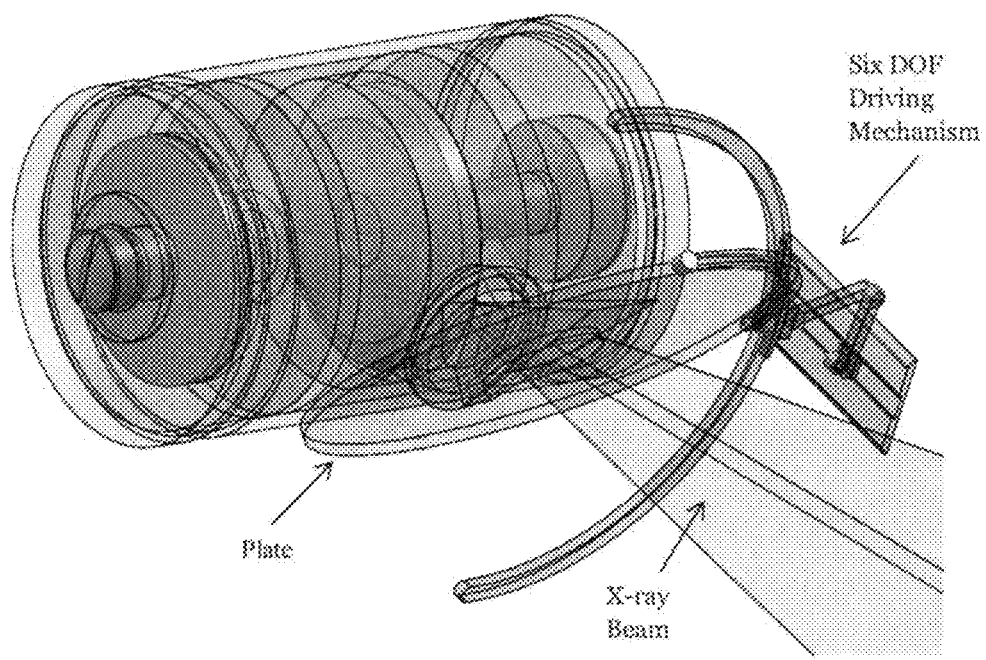

If the plate is slanted with respect to the central X-ray as FIGS. 12a and 12b, the shape of the X-ray beam can be made narrower. FIG. 12b is the zoomed image of the Six DOF Collimator in FIG. 12a. Since the plate can rotate in 3 DOF, the orientation of the shaped X-ray beam can be adjusted freely. Therefore, the Six DOF Collimator also can be used for the radiation therapy, in which it is essential to radiate only the ROI whose shape is not circular in general.

Multi Leaf Collimator for Breast CT Scanners

Figure 13A:
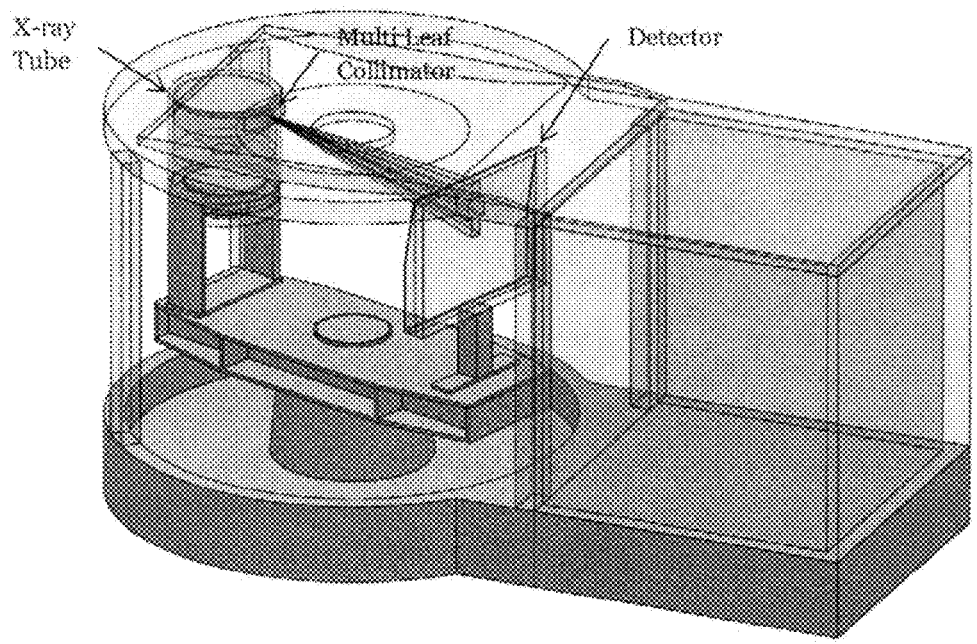
FIGS. 13a and 13b show a Multi Leaf Collimator attached to a breast CT scanner which partially blocks the X-ray cone beam to radiate only the ROI.
Figure 13B:
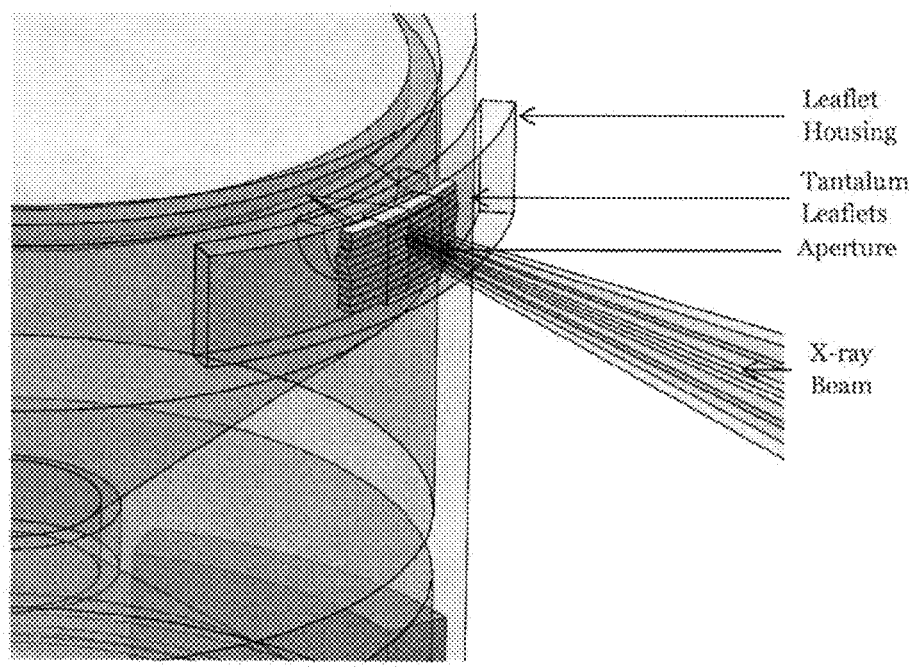
Figure 14A:
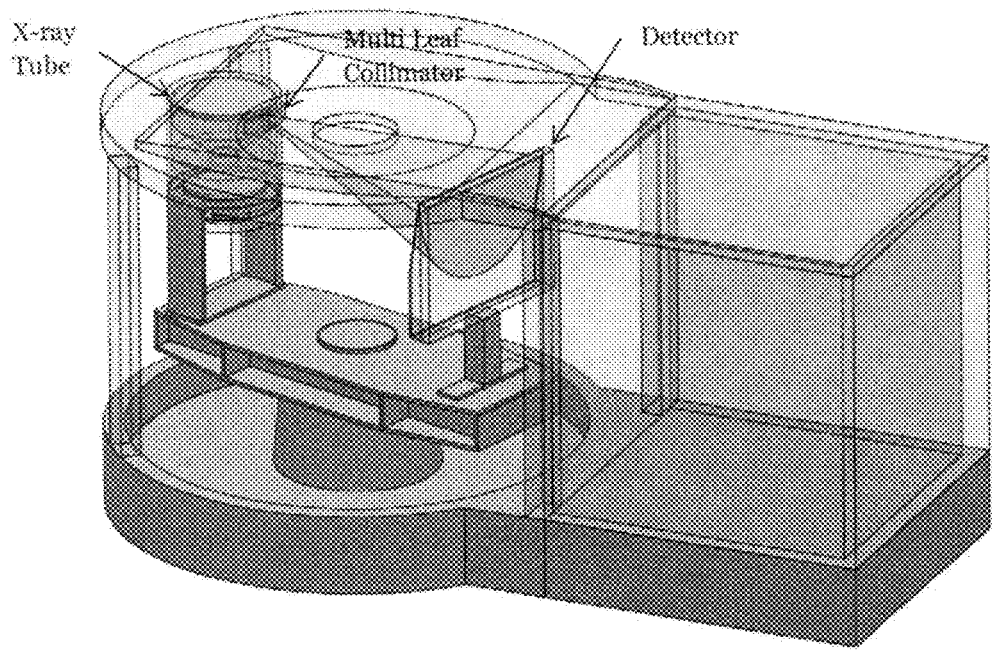
FIGS. 14a and 14b show the Multi Leaf Collimator attached to a breast CT scanner which does not block the X-ray cone beam.
Figure 14B:
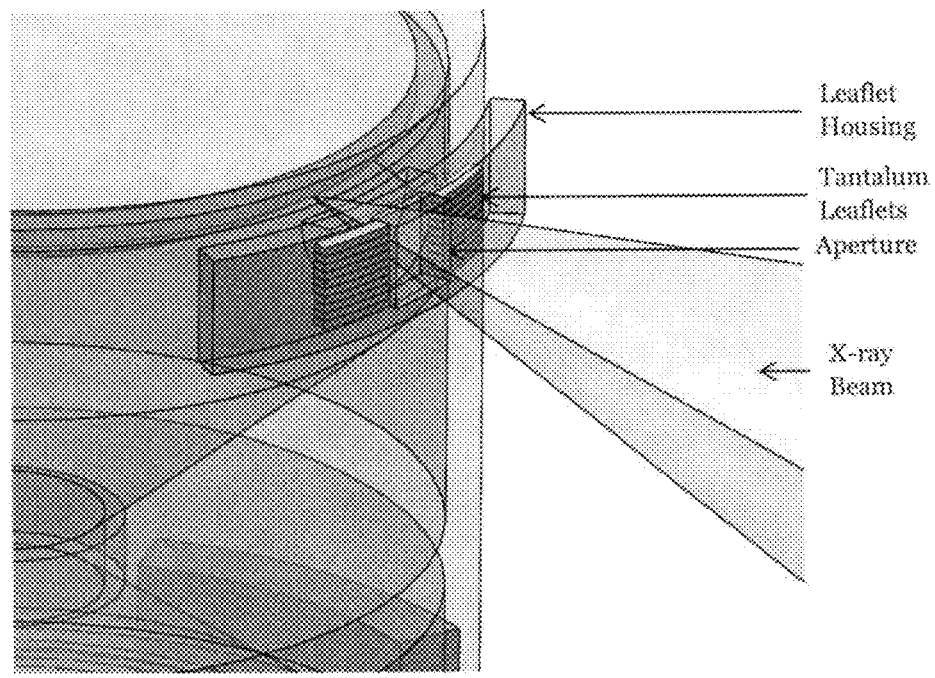
Figure 15A:
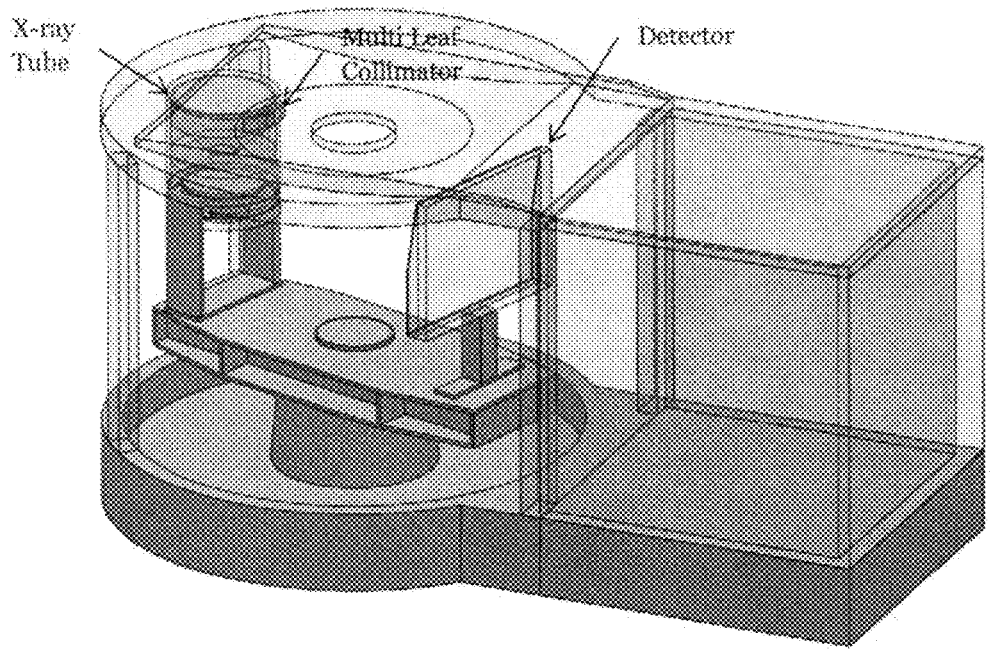
FIGS. 15a and 15b show a Multi Leaf Collimator attached to a breast CT scanner which completely blocks the X-ray cone beam.
Figure 15B:
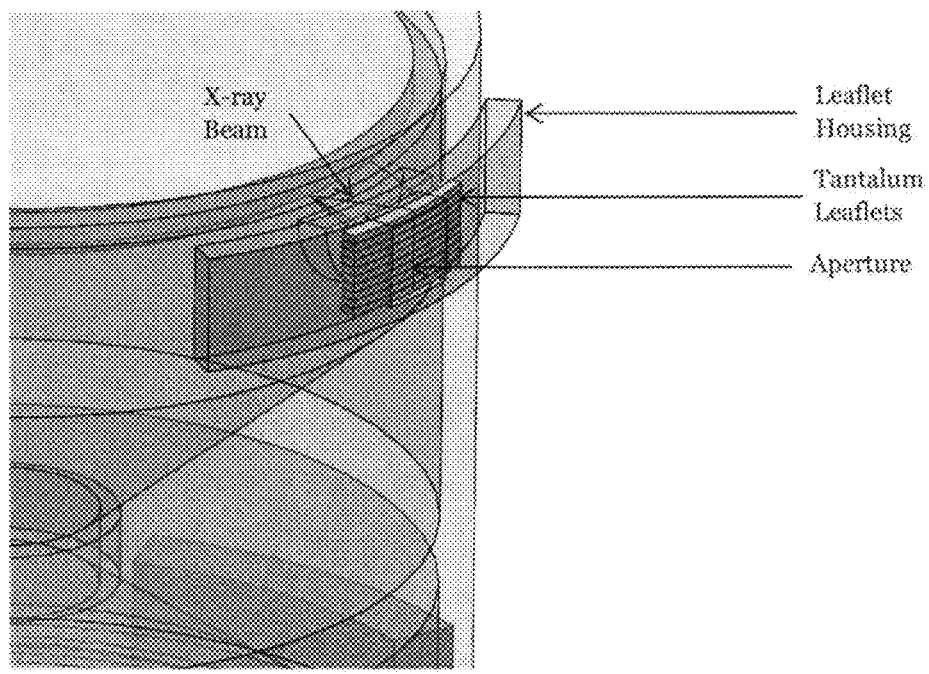

When performing breast CT scanning using breast CT scanners, a patient lies on a table with her chest down and back up unlike conventional CT scanning. There is a hole on the table of the breast CT scanner through which the breast hangs down. The X-ray tube and detector are placed under the table as shown in FIG. 13a to radiate only breasts. The Multi Leaf Collimator can also be used with breast CT scanners. As the case of mechanical CT scanners, the Multi Leaf Collimator is coupled to the X-ray tube and dynamically modulates the beam aperture while moving together with the X-ray tube. FIGS. 13a and 13b, FIGS. 14a and 14b, and FIGS. 15a and 15b show how the Multi Leaf Collimator works with the breast CT scanner by partially blocking, completely unblocking, and completely blocking the X-ray cone beam, respectively. Note that the X-ray cone beam from the X-ray tube is pre-collimated to radiate only the volume under the table. The projection data obtained by radiating only the ROI as FIGS. 13a and 13b can be used for the Interior Tomography while those obtained by blocking all X-rays at all source positions except some specific source locations as FIGS. 14a and 14b and FIGS. 15a and 15b can be used for the Sparse-view Tomography.

Six DOF Collimator for Breast CT Scanners

Figure 16:
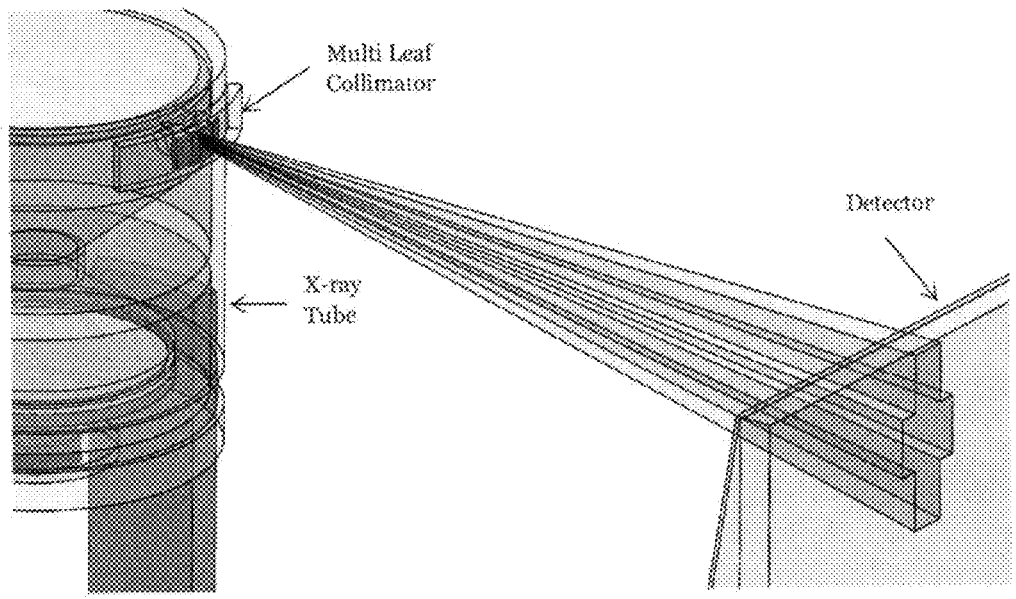
FIG. 16 shows a Six DOF Collimator attached to a breast CT scanner.
Figure 16:
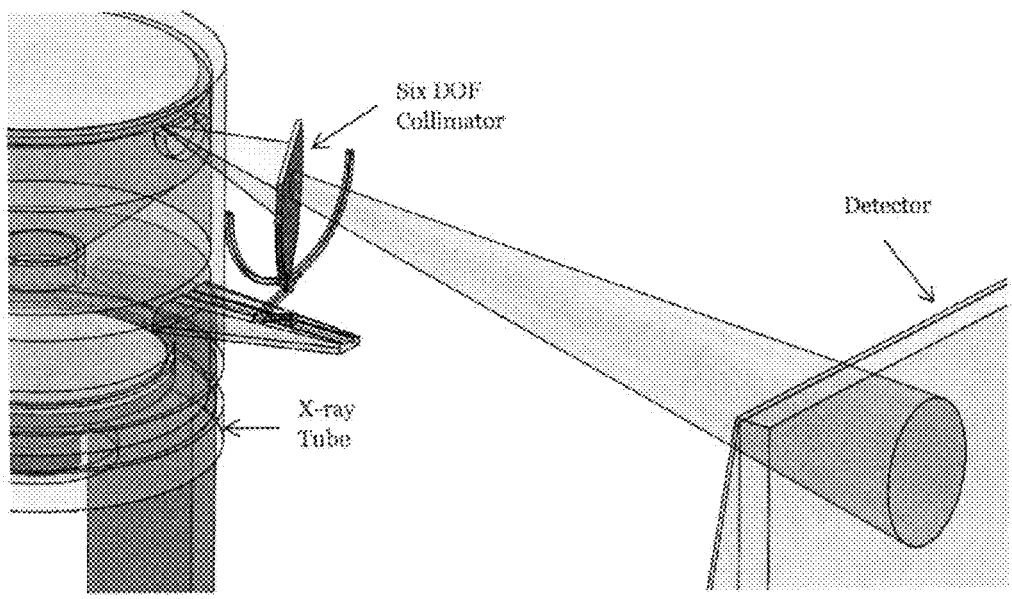

The Six DOF Collimator also can be used with breast CT scanners. FIG. 16 shows the details of the Six DOF Collimator attached to the X-ray tube of the breast CT scanner. By controlling the 3-D pose of the plate properly as the cases of mechanical CT scanners in FIGS. 9a and 9b, FIGS. 10a and 10b, FIGS. 11a and 11b, and FIGS. 12a and 12b, the Six DOF Collimator can work with the breast CT scanner for both the Interior Tomography and Sparse-view Tomography.

Simulation Studies

Figure 17:
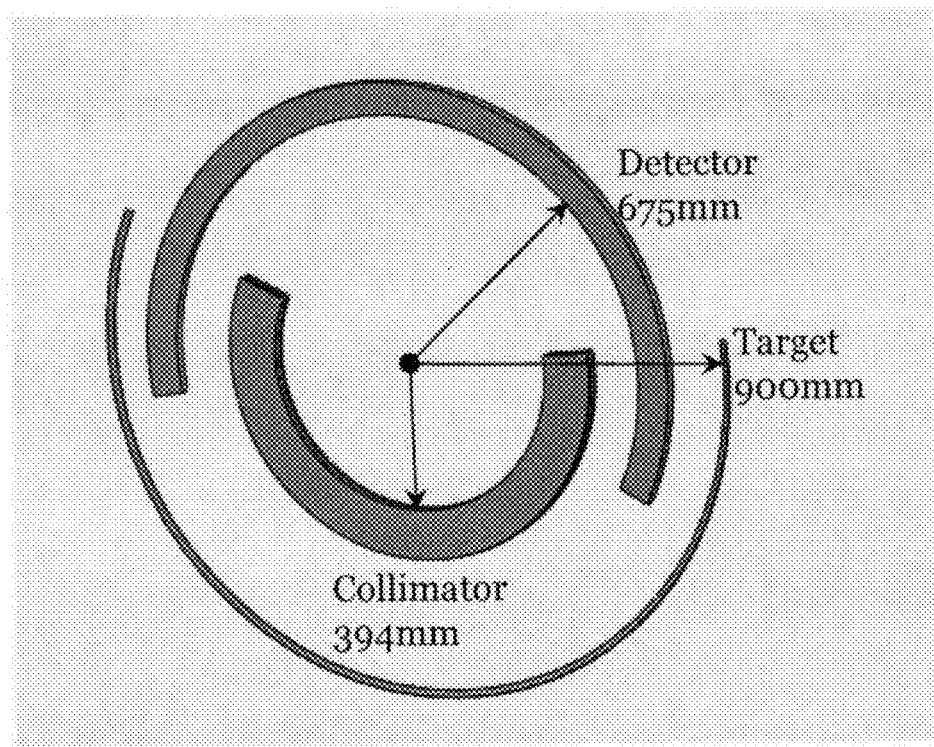
FIG. 17 shows the geometry of an EBCT scanner.
Figure 18A:
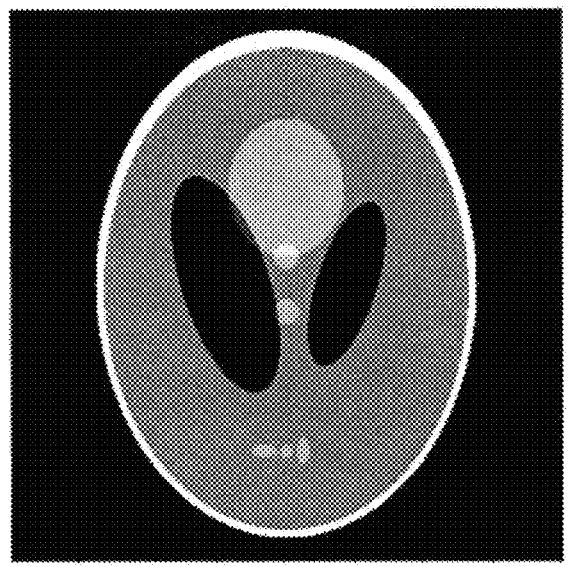
FIG. 18a shows the 2-D Shepp-Logan phantom used for simulation studies.
Figure 18B:
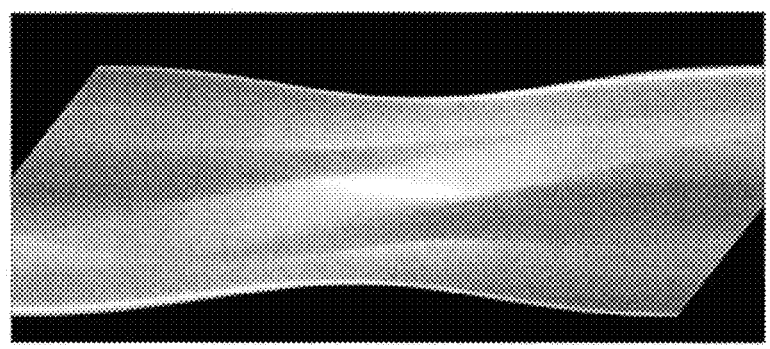
FIG. 18b shows a fan-beam sinogram obtained with the 2-D Shepp-Logan phantom by the EBCT scanner.
Figure 18C:
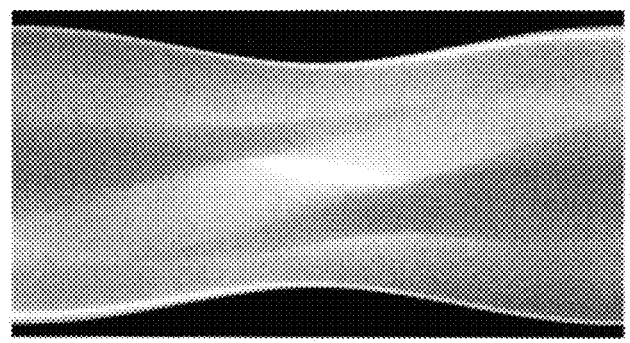
FIG. 18c shows a parallel-beam sinogram re-binned from the fan-beam sinogram in FIG. 18b.

We performed preliminary simulation studies to verify the feasibility of the Interior Tomography and Sparse-view Tomography using the EBCT geometry shown in FIG. 17. FIG. 18a shows the 2-D Shepp-Logan head phantom used in the simulation studies, which is a superposition of ellipses with distinct values. The phantom has been modified to increase the contrast between different tissues. With the EBCT geometry, the fan-beam projections were generated analytically. FIG. 18b shows the fan-beam sinogram whose horizontal and vertical coordinates represent source and detector positions, respectively. The parallel-beam sinogram is generated by re-binning the fan-beam sinogram with appropriate interpolation. FIG. 18c shows the re-binned parallel-beam sinogram with the bilinear interpolation.

Figure 19A:
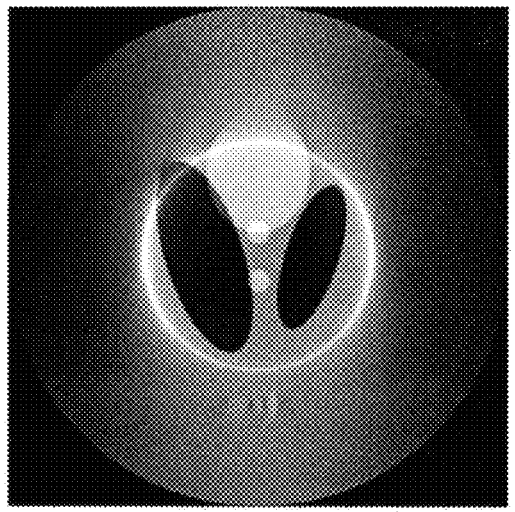
FIG. 19a shows the reconstruction result using the interior part of the sinogram in FIG. 18c by Simultaneous ART (SART).
Figure 19B:
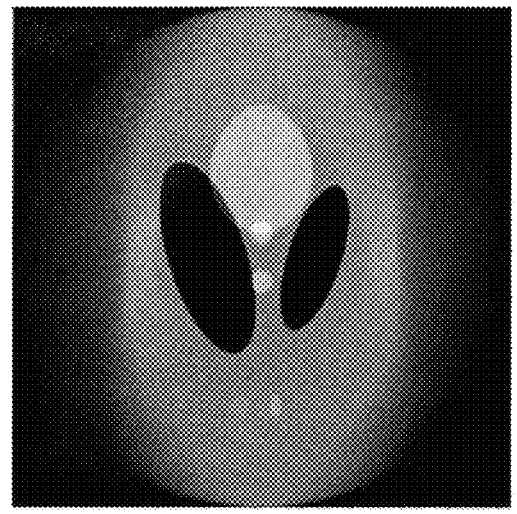
FIG. 19b shows the reconstruction result using the interior part of the sinogram in FIG. 18c by SART with TV minimization.
Figure 19C:
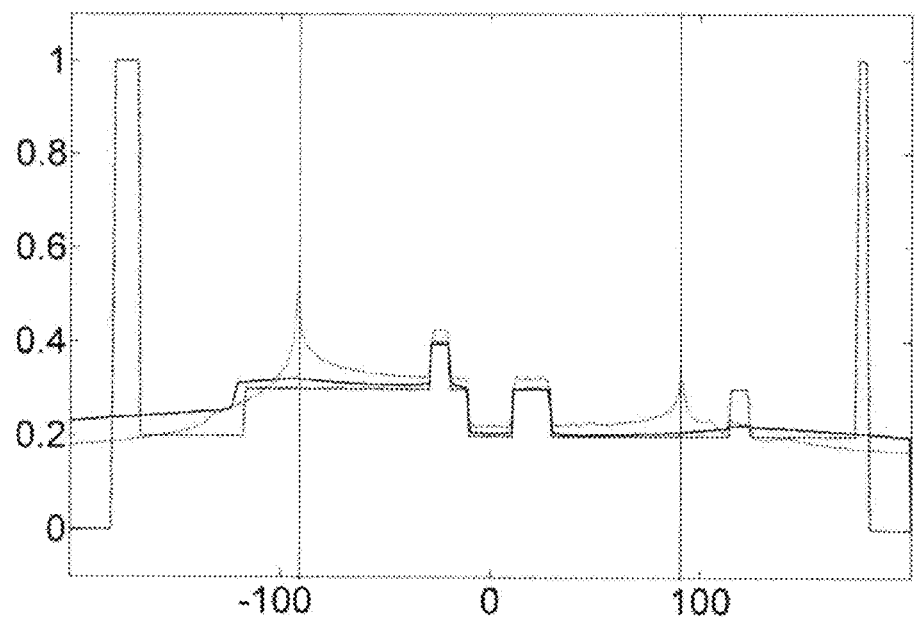
FIG. 19c shows the intensity profiles along the central vertical line of the phantom (dashed) and reconstructed results using the interior part of the sinogram in FIG. 18c by SART (dotted) and SART with TV minimization (solid).

The possibility of the use of truncated projections is first verified, which is obtained by the Dynamic Beam Collimator, for the accurate Interior Tomography. For simplicity, we truncated the parallel-beam sinogram by retaining the interior part instead of truncating the fan-beam sinogram actually obtained by the EBCT scanner. As a reconstruction algorithm, we used SART with TV minimization. FIG. 19a shows the reconstruction result by SART while FIG. 19b shows the reconstruction result by SART with TV minimization. The reconstruction result by SART is not quite accurate as the brighter ring caused by the discontinuity at the ROI boundary is clearly visible in FIG. 19a and the intensity profile of the central vertical line in FIG. 19c (dotted) is quite different from that of the phantom (dashed). On the contrary, the reconstruction by SART with TV minimization is quite accurate without a brighter ring at the ROI boundary as FIG. 19b and solid line in FIG. 19c show.

Figure 20D:
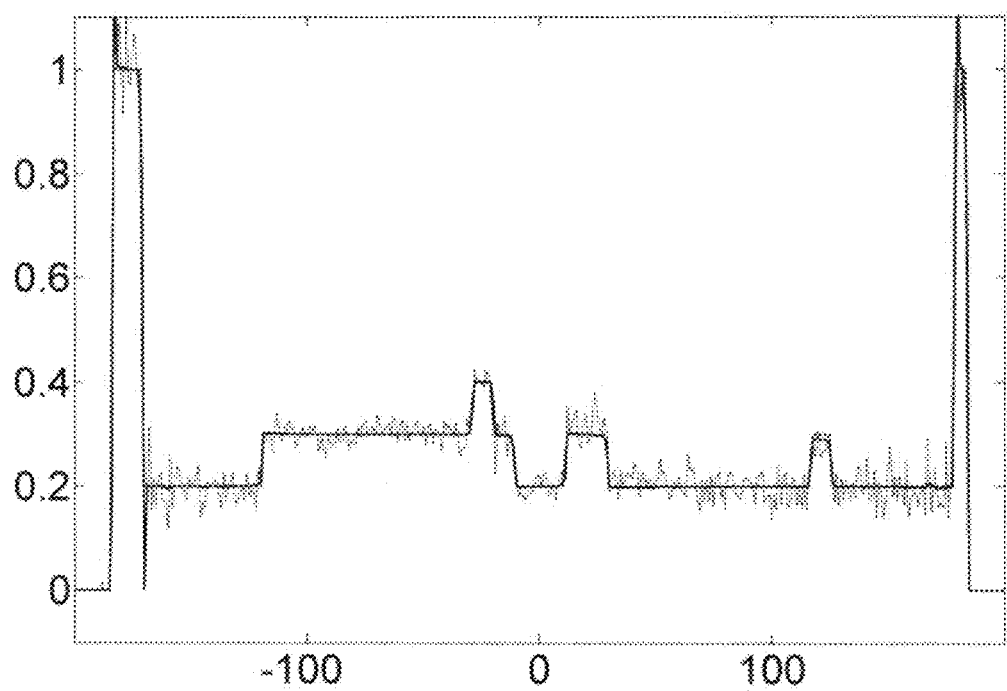
FIG. 20d shows the intensity profiles along the central vertical line of the phantom (dashed) and reconstructed results using the sinogram in FIG. 20a by SART (dotted) and SART with TV minimization (solid).

The feasibility of the use of the Sparse-view projections obtained by the Multi Slit Collimator for the accurate Sparse-view Tomography is then verified. The radius of Multi Slit Collimator is 880 mm. The angle of a single slit measured from the center is about 0.7°. The slit angle is determined so that a single 30° fan beam of the EBCT scanner can go through the slit completely. The total number of slits is 60. In this case, the radiation dose is 20% of the full-view projections of the EBCT scanner (((0.7°×60)/210°)×100=20%). FIG. 20a shows the fan-beam sinogram obtained with the Multi Slit Collimator. Each strip of the sinogram consists of 16 projections, one complete projection and 15 partial projections. Among 15 partial projections, two projections can be additionally treated as complete because they cover the head phantom completely. In this simulation study, 120 projections were used for reconstruction, 2 projections from each slit. FIG. 20b shows the reconstruction result by SART with 120 fan-beam projections where the streaking artifacts are clearly visible. FIG. 20c shows the reconstruction by SART with TV minimization with 120 fan-beam projections, which is quite satisfactory. As FIG. 20d shows, the reconstruction result by SART with TV minimization (solid) is far more accurate than SART (dotted) compared to the phantom (dashed).

Accordingly, in one embodiment, a computed tomography (CT) apparatus to perform a CT scan with a reduced radiation is disclosed. The apparatus includes: an X-ray source configured to direct a cone beam of X-rays toward a detector assembly with an object of interest situated between the X-ray source and the detector assembly; a dynamic beam collimator fixed in space and configured to dynamically limit the X-ray beam directed toward the object of interest, the dynamic beam collimator comprising a plurality of leaflets to block the cone beam of X-rays impinging upon the dynamic beam collimator, wherein a subset of the plurality of leaflets opens and closes to block or allow a portion of the cone beam of X-rays to reduce or increase a solid angle of the cone beam, wherein the cone beam of X-rays with the reduced solid angle is directed toward a predetermined portion of the object of interest; and the detector assembly configured to detect the directed cone beam of X-rays on a side opposite to the X-ray source after the cone beam of X-ray beams the reduced solid angle passes through the object of interest.

In one embodiment of the apparatus, the X-ray source includes: an electron gun to generate an electron beam; a beam steering assembly to steer the electron beam; and a target ring to receive the steered electron beam and generate an X-ray beam, wherein the beam steering assembly steers the electron beam onto different points around the target ring. In another embodiment, the apparatus further includes a multi-slit collimator coupled to the target ring, the multi-slit collimator configured with a plurality of slits circumferentially spaced at a predetermined spacing, wherein the multi-slit collimator limits the cone beam of X-rays by allowing the cone beam of X-rays to pass through only at a view angle determined by the spacing of the plurality of slits. In yet another embodiment, projection data as measured by the detector assembly is reconstructed to generate a volumetric data of linear attenuation coefficients. In yet another embodiment, reconstruction of the projection data includes: performing an interior tomography and a sparse-view tomography; and performing minimization of a metric on the measured and the reconstructed data. In a further embodiment, the metric comprises the total variation of the reconstructed data.

In another embodiment of a computed tomography (CT) apparatus to perform a CT scan with a reduced radiation, the apparatus includes: an X-ray source configured to direct a cone beam of X-rays toward a detector assembly with an object of interest situated between the source and the detector assembly; a multi-leaf collimator fixed with respect to the X-ray source and configured to dynamically limit the cone beam of X-rays directed toward the object of interest, the multi-leaf collimator comprising a plurality of leaflets to block impinging cone beam of X-rays, wherein a subset of the plurality of leaflets opens and closes to block or allow that portion of the cone beam of X-rays to reduce or increase a solid angle of the cone beam; wherein the X-ray beam with the reduced solid angle is directed towards a predetermined portion of the object of interest; and the detector assembly configured to detect the directed X-ray beam on a side opposite to the X-ray source after the X-ray beam with the reduced solid angle passes through the object of interest.

In one embodiment of the apparatus, the X-ray source, the multi-leaf collimator, and the detector assembly are fixed on a rotating gantry configured to rotate about the object of interest while the cone beam of X-rays with the reduced solid angle illuminates the predetermined portion of the object of interest to reconstruct an image of a particular portion of the object of interest with a preset resolution. In another embodiment, the apparatus further includes a 2-D collimator attached to a six degrees-of-freedom mechanism fixed with respect to the X-ray source, the 2-D collimator configured with a plate with a hole, wherein the six-degrees-of-freedom mechanism controls the 3-D pose of the plate to dynamically control the size and shape of an exiting X-ray beam directed toward the object of interest. In yet another embodiment, projection data as measured by the detector assembly is reconstructed to generate a volumetric data of linear attenuation coefficients. In yet another embodiment, reconstruction of the projection data includes: performing an interior tomography and a sparse-view tomography; and performing minimization of a metric on the measured and the reconstructed data. In yet another embodiment, the metric comprises the total variation of the reconstructed data.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter that is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A computed tomography (CT) apparatus to perform a CT scan with a reduced radiation dose, the apparatus comprising:
   an X-ray source configured to direct an X-ray fan beam toward a detector assembly with an object of interest situated between the X-ray source and the detector assembly, the X-ray source including
      an electron gun to generate an electron beam,
      a beam steering assembly to steer the electron beam, and
      a target ring to receive the steered electron beam and generate the X-ray fan beam;
   a dynamic beam collimator fixed with respect to the X-ray source and configured to dynamically modulate the X-ray fan beam directed toward the object of interest, the dynamic beam collimator comprising a plurality of leaflets to block the X-ray fan beam impinging upon the dynamic beam collimator,
   wherein the beam steering assembly steers the electron beam onto different points around the target ring and a subset of the plurality of leaflets opens and closes to block or allow a portion of the X-ray fan beam to modulate the X-ray fan beam by reducing or increasing a solid angle of the X-ray fan beam as the beam steering assembly steers the electron beam onto different points around the target ring,
   wherein the modulated X-ray fan beam is directed toward a predetermined portion of the object of interest; and
   the detector assembly configured to detect the modulated X-ray fan beam on a side of the object of interest opposite to the X-ray source after the modulated X-ray fan beam passes through the object of interest.

2. The apparatus of claim 1, further comprising
   a multi-slit collimator coupled to the target ring, the multi-slit collimator configured with a plurality of slits circumferentially spaced at a predetermined spacing,
   wherein the multi-slit collimator limits the X-ray fan beam by allowing the X-ray fan beam to pass through only at a view angle determined by the spacing of the plurality of slits.

3. The apparatus of claim 1, wherein projection data as measured by the detector assembly is reconstructed to generate a volumetric data of linear attenuation coefficients.

4. The apparatus of claim 3, wherein reconstruction of the projection data comprises:
   performing an interior tomography and a sparse-view tomography; and
   performing minimization of a metric on the measured and the reconstructed data.

5. The apparatus of claim 4, wherein the metric comprises the total variation of the reconstructed data.

6. A computed tomography (CT) apparatus to perform a CT scan with a reduced radiation dose, the apparatus comprising:
   an X-ray source configured to direct a fan beam of X-rays toward a detector assembly with an object of interest situated between the X-ray source and the detector assembly, the X-ray source comprising:
      an electron gun configured to generate an electron beam;
      a beam steering assembly configured to steer the electron beam; and
      a target ring, stationary with respect to the object of interest, configured to receive the steered electron beam and generate an X-ray beam,
      wherein the beam steering assembly is configured to steer the electron beam onto a plurality of points located on and around the target ring;
   a dynamic beam collimator, fixed with respect to the target ring, configured to dynamically limit the X-ray beam directed toward the object of interest, the dynamic beam collimator comprising a plurality of leaflets to block the fan beam of X-rays impinging upon the dynamic beam collimator,
   wherein a subset of the plurality of leaflets opens and closes to block or allow a portion of the fan beam of X-rays-to reduce a solid angle of the fan beam,
   wherein the fan beam of X-rays with the reduced solid angle is directed toward a predetermined portion of the object of interest; and
   the detector assembly configured to detect the directed fan beam of X-rays on a side of the object of interest opposite to the X-ray source after the fan beam of X-ray beams the reduced solid angle passes through the object of interest.

* * * * *